(12) United States Patent
Nakashima et al.

(10) Patent No.: US 8,202,456 B2
(45) Date of Patent: Jun. 19, 2012

(54) METHOD FOR PREPARING SUSTAINED RELEASE TABLET

(75) Inventors: Katashi Nakashima, Tonami (JP); Kazuo Kazama, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 302 days.

(21) Appl. No.: 12/514,330

(22) PCT Filed: Nov. 12, 2007

(86) PCT No.: PCT/JP2007/071919
§ 371 (c)(1),
(2), (4) Date: Dec. 16, 2009

(87) PCT Pub. No.: WO2008/059792
PCT Pub. Date: May 22, 2008

(65) Prior Publication Data
US 2010/0102474 A1    Apr. 29, 2010

(30) Foreign Application Priority Data
Nov. 13, 2006 (JP) ................... 2006-307244

(51) Int. Cl.
*B29C 43/02* (2006.01)
(52) U.S. Cl. ........ 264/112; 264/115; 264/117; 264/122; 424/470
(58) Field of Classification Search .................. None
See application file for complete search history.

(56) References Cited

U.S. PATENT DOCUMENTS

| 5,171,580 | A | 12/1992 | Iamartino et al. | |
| 5,695,781 | A | 12/1997 | Zhang et al. | |
| 6,177,102 | B1 * | 1/2001 | Chen et al. | 424/468 |
| 7,422,757 | B2 * | 9/2008 | Alander et al. | 424/464 |
| 2003/0108602 | A1 * | 6/2003 | Chu et al. | 424/465 |
| 2003/0180362 | A1 * | 9/2003 | Park et al. | 424/470 |
| 2003/0203024 | A1 | 10/2003 | Sako et al. | |

FOREIGN PATENT DOCUMENTS

| JP | 62 120315 | 6/1987 |
| JP | 63 215620 | 9/1988 |
| JP | 63 227519 | 9/1988 |
| JP | 04 501411 | 3/1992 |
| JP | 5 13132 | 2/1993 |
| JP | 9 20663 | 1/1997 |
| JP | 9 169645 | 6/1997 |
| JP | 9 315969 | 12/1997 |
| JP | 10 53524 | 2/1998 |
| JP | 11 514332 | 12/1999 |
| JP | 2003 534269 | 11/2003 |
| WO | 94 06414 | 3/1994 |

* cited by examiner

*Primary Examiner* — Mary F Theisen
(74) *Attorney, Agent, or Firm* — Oblon, Spivak, McClelland, Maier & Neustadt, L.L.P.

(57) ABSTRACT

Herein provided is a method for easily preparing a sustained release tablet which contains an orally administrable medicinal component, while maintaining the uniformity of the content of the medicinal component.
The method comprises mixing (1) a granulated product A obtained by granulating an excipient and an enteric coating agent while spraying thereon with a solution or a suspension containing an orally administrable medicinal component, with (2) a composition B containing a hydrogel-forming substance; and then compressing the resulting mixture into a tablet.

20 Claims, 1 Drawing Sheet

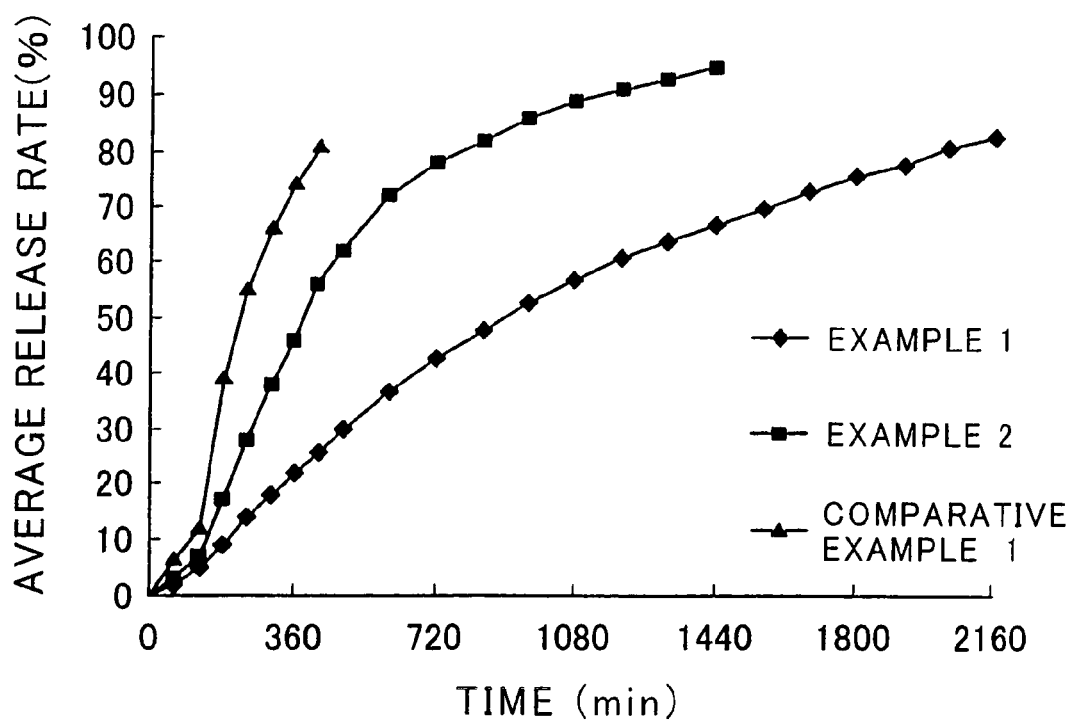

METHOD FOR PREPARING SUSTAINED RELEASE TABLET

TECHNICAL FIELD

The present invention relates to a simple method for the preparation of a sustained release tablet.

BACKGROUND ART

Some of the medicinal components orally administered cause harmful side effects such as nausea and vomiting, when they are adsorbed through stomach to thus cause an abrupt increase of the blood concentration thereof. Accordingly, there have been proposed various kinds of sustained release pharmaceutical preparations to be orally administered in order to prevent any abrupt increase of the blood concentration of the medicinal components thereof (See Patent Documents 1 to 4 specified below).

However, the methods disclosed in Patent Documents 1 to 3 for preparing such sustained release pharmaceutical preparations to be orally administered are quite complicated, which accordingly make the preparation of such sustained release pharmaceutical preparations quite difficult. In addition, the method for the production of the pharmaceutical preparation proposed in the Patent Document 4 is rather simple as compared with the methods for the production of other pharmaceutical preparations, but the former has a problem in that it is difficult to ensure the uniformity of the content of medicinal components in the pharmaceutical preparation and this accordingly makes the practice of the method difficult.

Patent Document 1: JP-A-9-020663
Patent Document 2: JP-A-9-169645
Patent Document 3: JP-A-9-315969
Patent Document 4: JP-A-10-053524

DISCLOSURE OF THE INVENTION

Subject to be Attained by the Invention

Accordingly, it is an object of the present invention to provide a method for the preparation of a tablet, which permits the easy preparation of such a tablet, while maintaining the uniformity of the content of medicinal components in the tablet, wherein the tablet can prevent any abrupt increase of the blood concentration of medicinal components to thus maintain a proper blood concentration.

Means for Attaining the Subject

The inventors of this invention have conducted various studies to solve the foregoing problems, and have found that a tablet having uniform content of medicinal components can be easily prepared by granulating, for instance, an excipient while spraying thereon with a solution or a suspension containing medicinal components to be used; mixing the resulting product with a hydrogel-forming substance; and then tabletting or compressing the resulting mixture into a tablet.

Specifically, the present invention relates to a method for preparing a tablet comprising the steps of:

mixing a granulated product A with a composition B containing a hydrogel-forming substance, said granulated product A being obtained by granulating an excipient and an enteric coating agent, while spraying thereon a solution or a suspension containing an orally administrable medicinal component; and then compressing the resulting mixture into a tablet.

Effects of the Invention

The present invention permits the easy preparation of a sustained release tablet containing orally administrable medicinal components, while maintaining the uniformity of the content of the medicinal components in the tablets.

BEST MODE FOR CARRYING OUT THE INVENTION

1. Granulated Product A

The granulated product A used in the preparation method according to the present invention can be obtained by granulating an excipient and an enteric coating agent while spraying thereon with a solution or a suspension containing orally administrable medicinal components.

When eliminating drawbacks by mixing an enteric coating agent with a medicinal component whose absorption through the stomach is not preferred or a medicinal component which is unstable to the acid, the production method according to the present invention is useful for the improvement of the uniformity of the content of the medicinal component and for further making the production of tablets easier.

Examples of such medicinal components whose absorption through the stomach is not preferred include non-steroidal anti-inflammatory drugs such as aspirin, diclofenac, indometacin, ibuprofen, ketoprofen, naproxen, and piroxicam; cerebral circulation-improving drugs such as ifenprodil, ibudilast, dihydroergotoxine, and nilvadipine.

Examples of the foregoing medicinal components which are unstable to the acid are erythromycin, levothyroxine, furosemide, pirenzepine, pravastatin, lansoprazole, ampicillin, carbenicillin, cefalotin, cefaloridine, cefotaxime, and diltiazem.

To spray the foregoing medicinal components on, for instance, an excipient, they are dissolved or suspended in water, ethanol or a mixed solvent thereof. Preferred are aqueous ethanol mixed solvents having an ethanol concentration ranging from 50 to 90% by mass. The concentration of the medicinal component in the solution preferably ranges from 5 to 50% by mass, more preferably 10 to 40% by mass and still more preferably 15 to 30% by mass. Moreover, when the medicinal component is suspended in such a solvent, it is preferred to add a suspending agent. The method for spraying such a solution of a suspension is not restricted to any particular one insofar as it can be used in the preparation of a pharmaceutical preparation.

The enteric coating agent is an additive for preparing a medicinal product, which shows such characteristic properties that it is not dissolved in the stomach, but is dissolved or decomposed in the intestinal tract and usable herein may be one which never causes any change when it is brought into contact with an artificial gastric juice such as an HCl solution having a pH of 1 over at least two hours and which can be dissolved or decomposed within 30 minutes when it is subsequently introduced into an artificial intestinal liquid such as a $KH_2PO_4$ buffer solution having a pH value of 6.8. Specific examples thereof include hydroxypropyl-methyl cellulose phthalate, hydroxymethyl cellulose acetate succinate, carboxymethyl-ethyl cellulose, methacrylic acid copolymer L, and methacrylic acid copolymer S and preferably used herein include, for instance, hydroxypropyl-methyl cellulose acetate succinates (such as Shin-Etsu AQOAT AS-MF available from Shin-Etsu Chemical Co., Ltd.). The concentration of the enteric coating agent present in the granulated product is preferably not more than 50% by mass, more preferably 5 to 40% by mass and further preferably 10 to 35% by mass.

The excipient usable in the present invention is not restricted to any specific one inasmuch as it can be used in the production of a pharmaceutical preparation containing a medicinal agent and examples thereof include those disclosed in, for instance, Dictionary of Drug Additives (edited by Nippon Drug Additive Association, published by Yakuji Nippo Publishing Co., Ltd. (2005)). More specifically, there may be listed, for instance, saccharides such as lactose, and glucose; sugar alcohols such as D-sorbitol and mannitol; celluloses such as crystalline cellulose; and starches such as corn starch and partially pregelatinized starch. Preferably used in the present invention are, for instance, lactose products [such as lactose monohydrate 200 mesh (available from Lactose New Zealand Company) and Dilactose S (available from Freund Corporation)]. The concentration of the excipient present in the granulated product is preferably not less than 30% by mass, more preferably 40 to 90% by mass and further preferably 45 to 80% by mass.

It is preferred in the present invention that the average particle size of the granulated product A ranges, for instance, from 50 to 300 µm, preferably 100 to 200 µm. This is because if the average particle size thereof exceeds 300 µm, the resulting granulated product can easily be handled, but if it is too large, the granulated product may easily be separated from the powdery component subsequently added thereto. In this connection, the average particle size of the granulated product is determined by, for instance, the JIS Sieve-Classification Method (this is a method for determining the particle size and particle size distribution using a standard sieve and the particle size and particle size distribution as determined by this method are expressed in terms of the mesh or opening (µm) of the sieve used and the rate of the residue on sieve (over size) or the plus sieve, and the amount of passage (under size) or minus sieve, relative to the total amount of the granulated product).

To the granulated product A, there can be added components other than the medicinal component, the enteric coating agent and the excipient, inasmuch as they never adversely affect the effects of the present invention.

In the meantime, it is preferred that the granulated product A is free of any hydrogel-forming substance as will be described later, but if the granulated product includes such a hydrogel-forming substance, the hydrogel-forming substance is preferably incorporated into the granulated product A in an amount of not more than 10% by mass and more preferably not more than 5% by mass (0 to 5% by mass) relative to the amount of the enteric coating agent, while taking into consideration the easiness of the production thereof.

Examples of the methods for the preparation of the granulated product A include the stirring-granulation technique, the extrusion-granulation technique, the fluidized layer (bed)-granulation technique, the rolling fluidized layer (bed)-granulation technique, and the spraying-granulation technique, with the fluidized layer (bed)-granulation technique being preferably used herein.

The granulated product A used in the present invention is preferably dried after the granulation from the viewpoint of the stability of the drug component and the easiness of the tablet production. The drying method is not restricted to any specific one insofar as it can be used for the production of a drug or a pharmaceutical preparation.

2. Mixing and Compression or Tabletting of Granulated Product A with Composition B The production method according to the present invention is characterized in that it comprises the steps of mixing the granulated product A with the composition B and compressing the resulting mix. The composition B is characterized in that it comprises a hydrogel-forming substance.

The hydrogel-forming substance is a substance which can get swollen through the absorption of a solvent, in which the resulting colloidal particles can be connected together to form a three-dimensional network structure and to thus form a jelly-like substance which loses the flow properties. When designing a pharmaceutical preparation, the hydrogel-forming substance can be used as a base having a sustained releasing ability. Examples of such hydrogel-forming substances preferably used herein include gum Arabic, sodium alginate, alginic acid propylene glycol ester, carbomer, xanthan gum, carob bean gum, carboxymethyl cellulose, sodium carboxymethyl cellulose, guar gum, gelatin, polyvinyl alcohol, methyl cellulose, hydroxypropyl cellulose, hydroxypropylmethyl cellulose, and polyethylene oxide, but preferably used in the present invention are, for instance, hydroxypropylmethyl cellulose products (such as Metholose 60SH-4000 available from Shin-Etsu Chemical Co., Ltd.). The concentration of the hydrogel-forming substance in the ultimately produced tablet preferably ranges from 5 to 70% by mass, more preferably 10 to 60% by mass, further preferably 20 to 60% by mass and particularly preferably 30 to 60% by mass, while taking into consideration the ability thereof to continuously release a desired medicinal component and the easiness of the tablet-production.

Composition B may further comprise other components in addition to the hydrogel-forming substance inasmuch as they never adversely affect the intended effects of the present invention. Examples of such other additives are a lubricant and an excipient.

The lubricant which can be incorporated into Composition B in combination with the hydrogel-forming substance is not restricted to any specific one inasmuch as it can be used for the production of a pharmaceutical preparation and it may be selected from a variety of lubricants. Examples of such lubricants can arbitrarily be selected from those disclosed in, for instance, Dictionary of Drug Additives. Specific examples thereof suitably used herein are magnesium stearate, calcium stearate, talc, and fats and oils such as hardened oils and sucrose esters of fatty acids, with magnesium stearate being preferably used in the invention.

The excipients are not restricted to particular ones inasmuch as they can be used for the production of a pharmaceutical preparation, but preferred are those having a granular shape from the viewpoint of, for instance, the compression ability. Specific examples thereof are Dilactose (available from Freund Corporation).

In this respect, it is preferred that any enteric coating agent is not incorporated into Composition B, but if incorporating an enteric coating agent into Composition B, the amount of the enteric coating agent is preferably not more than 10% by mass and more preferably not more than 5% by mass (0 to 5% by mass) relative to the amount of the hydrogel-forming substance used.

The method for mixing the granulated product A with Composition B is not restricted to any specific one insofar as it can be used for the production of a pharmaceutical preparation, but it is preferred to use a mixing machine in which these components are admixed together while repeating the alternating counter flow dropping due to the action of the gravitational force and the centrifugal force generated when rotating the container.

The method for compressing or tabletting the mixture of the granulated product A with Composition B is not restricted to any particular one, inasmuch as it can be used for the production of a pharmaceutical preparation. The pressure for the compression of the mix used in the preparation of a tablet preferably ranges from about 200 to about 1,000 kgf and further preferably 300 to 800 kgf for a tablet having a diameter ranging from about 7 to 8 mm.

3. Coating

The production method according to the present invention preferably comprises the step of coating the tablet obtained after the tabletting step with Composition C.

Composition C herein used comprises a water-soluble film-coating agent, a coloring agent and/or a gloss-imparting agent. As such water-soluble film-coating agents, there may be listed, for instance, hydroxypropyl-methyl cellulose (such as TC-5RW available from Shin-Etsu Chemical Co., Ltd.) and hydroxypropyl cellulose. Examples of such coloring agents include titanium oxide (such as Titanium Oxide NA61 available from Toho Titanium Co., Ltd.), iron sesquioxide, and yellow iron sesquioxide. Examples of such gloss-imparting agents include carnauba wax (Polishing Wax-101 available from Freund Corporation).

The production method according to the present invention is effectively applied to the production of a tablet which can maintain a desired blood concentration of the medicinal component thereof over a long period of time, in particular, effectively applied to the production of a sustained release tablet showing such pH-dependent sustained release properties that the release of the medicinal component can be suppressed in an artificial gastric juice (First Liquid for the disintegration test specified in Japanese Pharmacopoeia, $14^{th}$ Revision, pH 1.2), while the medicinal component can be released in an artificial intestinal tract liquid (Second Liquid for the disintegration test specified in Japanese Pharmacopoeia, $14^{th}$ Revision, pH 6.8) at a predetermined rate over a long period of time. The pH-dependent sustained release tablet shows such effective component-release properties, in the living body, that the release of an effective component is suppressed in the stomach to thus control the occurrence of any abrupt increase of the blood concentration of the component, while the tablet can gradually be hydrated and eroded, in the duodenum and the downstream thereof, when the surface of the tablet comes into contact with the liquid within the digestive tract and the wall thereof and as a result, the medicinal component can be released in small portions and continuously absorbed by the living body through the wall of the digestive tract.

The present invention will hereunder be described in more detail with reference to the following Examples, but the scope of the present invention is not restricted to these specific Examples at all.

Example 1

TABLE 1

| Component | Amt. of Component per Tablet (mg) |
|---|---|
| Ibudilast | 10.0 |
| Lactose monohydrate | 24.8 |
| Shin-Etsu AQOAT AS-MF | 15.0 |
| Metholose 60SH-4000 | 70.0 |
| Magnesium stearate | 0.2 |
| TC-5RW | 2.7 |
| Titanium Oxide NA61 | 0.3 |
| Polishing Wax-103 | 0.001 |
| Total Amt. | 123.001 |

In a fluidized bed granulation device (Flow Coater, FBG-5, available from Freund Corporation), a mixture of lactose [lactose monohydrate having a particle size of 200 mesh (available from Lactose New Zealand Company)] and hydroxypropyl-methyl cellulose acetate succinate [Shin-Etsu AQOAT AS-MF (available from Shin-Etsu Chemical Co., Ltd.)] was sprayed with a solution (ethanol (95%):water:ibudilast=67:13:20 (ratio by mass) obtained by dissolving ibudilast in a mixed solvent of ethanol (95%) and water, thereby forming granulated product. The resulting granulated product was then classified by passing it through a sieve of 850 μm to thus give ibudilast-containing granules. The ibudilast-containing granules and hydroxypropyl-methyl cellulose [Metholose 60SH-4000 (available from Shin-Etsu Chemical Co., Ltd.)] were mixed in a V-shaped mixer (FM-SVM-20 available from Tsukasa Industry Co., Ltd.), then magnesium stearate was added to the resulting mixture and they were further mixed together. The resulting mixture was compressed into coating-free tablets using a full automatic small-sized tabletting machine (HT-AP18SS-II Model available from Hata Ironworks Co., Ltd.) provided with a circular mortar and pestle (the diameter and radius of curvature thereof are 7 mm and 9 mm, respectively). The coating-free tablets thus obtained were coated with hydroxypropyl-methyl cellulose [TC-5RW available from Shin-Etsu Chemical Co., Ltd.] and titanium oxide NA61 (available from Toho Titanium Co., Ltd.) using a coating machine (HCT-MINI available from Freund Corporation.), thereby preparing film-coated tablets. Then, carnauba wax [Polishing Wax-103 (available from Freund Corporation.)] was added to the film-coated tablets thus obtained in the same coating machine used above and then the tablets were subjected to a polishing treatment to thus form tablets each containing 10 mg of ibudilast.

Example 2

TABLE 2

| Component | Amt. of Component per Tablet (mg) |
|---|---|
| Ibudilast | 10.0 |
| Lactose monohydrate | 24.8 |
| Shin-Etsu AQOAT AS-MF | 15.0 |
| Dilactose S | 40.0 |
| Metholose 60SH-4000 | 30.0 |
| Magnesium stearate | 1.2 |
| TC-5RW | 2.7 |
| Titanium Oxide NA61 | 1.3 |
| Polishing Wax-103 | 0.001 |
| Total Amt. | 123.001 |

Ibudilast-containing granules were prepared according to the same method used in Example 1. The ibudilast-containing granules, lactose [Dilactose S (available from Freund Corporation.)] and hydroxypropyl-methyl cellulose [Metholose 60SH-4000 (available from Shin-Etsu Chemical Co., Ltd.)]

were mixed in a V-shaped mixer (FM-SVM-20 available from Tsukasa Industry Co., Ltd.), then magnesium stearate was added to the resulting mixture and they were further mixed together. The resulting mixture was compressed into coating-free tablets using a full automatic small-sized tabletting machine (HT-AP18SS-II Model available from Hata Ironworks Co., Ltd.) provided with a circular mortar and pestle (the diameter and radius of curvature thereof are 7 mm and 9 mm, respectively). The coating-free tablets thus obtained were coated with hydroxypropyl-methyl cellulose [TC-5RW available from Shin-Etsu Chemical Co., Ltd.] and titanium oxide NA61 (available from Toho Titanium Co., Ltd.) using a coating machine (HCT-MINI available from Freund Corporation.) to thus prepare film-coated tablets. Then, carnauba wax [Polishing Wax-103 (available from Freund Corporation.)] was added to the film-coated tablets thus obtained in the same coating machine used above and then the tablets were subjected to a polishing treatment to thus form tablets each containing 10 mg of ibudilast.

Comparative Example 1

There were sufficiently mixed 10 g of ibudilast, 60 g of lactose [lactose monohydrate having a particle size of 200 mesh (available from Lactose New Zealand Company)], 20 g of hydroxypropyl-methyl cellulose [Metholose 60SH-4000 (available from Shin-Etsu Chemical Co., Ltd.)] and 30 g of hydroxypropyl-methyl cellulose acetate succinate [Shin-Etsu AQOAT AS-MF (available from Shin-Etsu Chemical Co., Ltd.)], 18.2 g of ethanol (95%) was then added to the resulting mixed powder, followed by the sufficient mixing and the subsequent drying thereof at a temperature ranging from 40 to 50° C. The dried product was subjected to a particle size adjustment using a sieve having a mesh size of 850 μm, then magnesium stearate was added to the classified product and the resulting mixture was compression-molded with a tablet-molding pestle (diameter: 7 mm) to thus give desired tablets each having a weight of 120 mg and containing 10 mg of ibudilast per tablet.

Test Example 1

Release tests were carried out using the tablets prepared in Examples 1 and 2 and the tablet prepared in Comparative Example 1 (one tablet each), according to the release test method No. 1 specified in Japanese Pharmacopoeia, 14$^{th}$ Revised Edition. The release test for each tablet was carried out using 6 vessels. In this case, the number of rotations was set at 100 rpm, and the test liquids used herein and maintained at 37° C. were the first liquid (hereunder abbreviated as "artificial gastric juice") and the second liquid (hereunder abbreviated as "artificial intestinal tract liquid") for the disintegration test as specified in Japanese Pharmacopoeia, 14$^{th}$ Revised Edition (500 mL each). The release test were carried out using the artificial gastric juice during the term starting from the initiation of the release test to 2 hours after the initiation and the release tests were continuously carried out during the term on and after 2 hours from the initiation of the release test, while the artificial intestinal tract liquid as another test liquid was substituted for the artificial gastric juice. In these release tests, there was used an automatic release test machine. Each test liquid was collected from each vessel at predetermined intervals, then filtered and introduced into a spectrophotometer to thus determine the difference in the absorbance between those observed at a measuring wavelength of 319 nm and a reference wavelength of 340 nm. After the determination of the difference in absorbance, the test liquid was immediately returned to the original vessel. The rate of released ibudilast in the test liquid was calculated on the basis of the difference in absorbance thus determined. FIG. 1 shows the rate of released ibudilast observed for each pharmaceutical preparation as a function of elapsed time. As a result, it was found that the tablets prepared in Examples 1 and 2, each of which had a content of hydrogel-forming substance of not less than 20% by mass showed excellent sustained medicinal component-release properties as compared with those observed for the tablet prepared in Comparative Example 1.

Test Example 2

The tablets prepared in Examples 1 and 2 were packed in brown-colored glass bottles and then stored at 40° C. over 6 months. The rates of ibudilast released from each tablet before and after the storage were determined according to the following method:

The release tests were carried out using the foregoing tablets (one tablet each) according to the release test method No. 1 as specified in Japanese Pharmacopoeia, 14$^{th}$ Revised Edition. The release test for each tablet was carried out using 6 vessels. In this connection, the number of rotations was set at 100 rpm, and the test liquids used herein and maintained at 37° C. were the artificial gastric juice and the artificial intestinal tract liquid (900 mL each). In these release tests, there was used an automatic release test machine. Each test liquid was collected from each vessel after 2 hours from the initiation of the release test under the test conditions encountered when using the artificial gastric juice and at intervals of a predetermined time under the test conditions encountered when using the artificial intestinal tract liquid, then filtered and supplied to a spectrophotometer to thus determine the difference in the absorbance between those observed at a measuring wavelength of 319 nm and a reference wavelength of 340 nm. After the determination of the difference in absorbance, each test liquid was immediately returned to the original vessel. The rate of released ibudilast in the test liquid was calculated on the basis of the difference in absorbance thus determined.

The following Table 3 shows the average rates of ibudilast released from the tablets prepared in Examples 1 and 2 in the artificial gastric juice.

TABLE 3

Average Rates of Ibudilast Released from the Tablets Prepared in Examples 1 and 2 in the Artificial Gastric Juice

|  | Prior to Storage (%) | After Storage (%) |
|---|---|---|
| Example 1 | 5 | 6 |
| Example 2 | 6 | 8 |

The results listed in the foregoing Table 3 indicate that the rates of ibudilast released from the tablets prepared in Examples 1 and 2 in the artificial gastric juice did not show any substantial change before and after the storage thereof and that both of these tablets showed excellent storage stability.

Test Example 3

The tablets prepared in Examples 1 and 2 and Comparative Example 1 were evaluated or inspected for the uniformity of the ibudilast-contents according to the content-uniformity test specified in Japanese Pharmacopoeia, 14$^{th}$ Revised Edition. The ibudilast-content in each tablet was determined according to the PLC technique. The following Table 4 shows the judged values (%) of these tablets:

TABLE 4

|  | Judged Value (%) |
| --- | --- |
| Example 1 | 1.9 |
| Example 2 | 1.9 |
| Comparative Example 1 | 21.4 |

The judged values observed for the tablets prepared in Examples 1 and 2 are in conformity with the reference value for judgment (more specifically less than 15.0%) as specified in the content-uniformity test disclosed in Japanese Pharmacopoeia, $14^{th}$ Revised Edition although these tablets contain a large amount (not less than 20% by mass) of a hydrogel-forming substance and as a result, it was found that the ibudilast-content in each tablet was uniform. On the other hand, it was found that the tablet prepared in Comparative Example 1, which had been prepared by compressing a simple mixture free of any granulation treatment, showed a judged value higher than the foregoing reference level although the content of a hydrogel-forming substance was low (16.7% by mass) as compared with those of the tablets prepared in Examples 1 and 2 and that the ibudilast-content in the tablet was non-uniform.

FIG. 1 shows the results obtained when the release rate of ibudilast was monitored over 90 hours (2160 minutes). The data shown in this FIGURE clearly indicate that the tablet prepared in Comparative Example 1 showed a high initial drug-release rate as compared with those observed for the tablets prepared in Examples 1 and 2.

INDUSTRIAL APPLICABILITY

The present invention thus permits the easy production of a sustained release tablet which contains an orally administrable medicinal component, while maintaining the uniformity of the content of the medicinal component.

BRIEF DESCRIPTION OF THE DRAWING

FIG. 1 shows the relation between the average release rate of each tablet and the time elapsed.

What is claimed is:

1. A method for preparing a tablet comprising:
   mixing a granulated product A with a composition B containing a hydrogel-forming substance, said granulated product A being obtained by granulating an excipient and an enteric coating agent, while spraying thereon a solution or a suspension containing an orally administrable medicinal component; and then
   compressing the resulting mixture into a tablet.

2. The method of claim 1, wherein said composition B comprises an excipient.

3. The method of claim 1, wherein said granulated product A is dried and then mixed with said composition B, before the compressing step.

4. The method of claim 1, further comprising a step of coating the tablet with a composition C comprising a water-soluble film-coating agent and/or a coloring agent.

5. The method of claim 2, further comprising a step of coating the tablet with a composition C comprising a water-soluble film-coating agent and/or a coloring agent.

6. The method of claim 3, further comprising a step of coating the tablet with a composition C comprising a water-soluble film-coating agent and/or a coloring agent.

7. The method of claim 2, wherein said granulated product A is dried and then mixed with said composition B, before the compressing step.

8. The method of claim 7, further comprising a step of coating the tablet with a composition C comprising a water-soluble film-coating agent and/or a coloring agent.

9. The method of claim 1, wherein said orally administrable medicinal component is a non-steroidal anti-inflammatory drug selected from the group consisting of aspirin, diclofenac, indometacin, ibuprofen, ketoprofen, naproxen, and piroxicam.

10. The method of claim 1, wherein said orally administrable medicinal component is a cerebral circulation-improving drug selected from the group consisting of ifenprodil, ibudilast, dihydroergotoxine, and nilvadipine.

11. The method of claim 1, wherein said orally administrable medicinal component is selected from the group consisting of erythromycin, levothyroxine, furosemide, pirenzepine, pravastatin, lansoprazole, ampicillin, carbenicillin, cefalotin, cefaloridine, cefotaxime, and diltiazem.

12. The method of claim 1, wherein the solvent comprised in said solution or suspension is water, ethanol, or a mixed solvent thereof.

13. The method of claim 1, wherein the solvent comprised in said solution or suspension is an aqueous ethanol mixed solvent with an ethanol concentration ranging from 50 to 90% by mass.

14. The method of claim 1, wherein the concentration of said orally administrable medicinal component in said solution or suspension ranges from 5 to 50% by mass.

15. The method of claim 1, wherein the concentration of said orally administrable medicinal component in said solution or suspension ranges from 15 to 30% by mass.

16. The method of claim 1, wherein said enteric coating agent is selected from the group consisting of hydroxypropyl-methyl cellulose phthalate, hydroxymethyl cellulose acetate succinate, carboxymethyl-ethyl cellulose, methacrylic acid copolymer L, methacrylic acid copolymer S, and hydroxypropyl-methyl cellulose acetate succinate.

17. The method of claim 1, wherein the average particle size of the granulated product A ranges from 50 to 300 µm.

18. The method of claim 1, wherein said granulated product A is prepared by a process selected from the group consisting of a stirring-granulation technique, an extrusion-granulation technique, a fluidized layer (bed)-granulation technique, a rolling fluidized layer (bed)-granulation technique, and a spraying-granulation technique with a fluidized layer (bed)-granulation technique.

19. The method of claim 1, wherein said hydrogel-forming substance is selected from the group consisting of gum Arabic, sodium alginate, alginic acid propylene glycol ester, carbomer, xanthan gum, carob bean gum, carboxymethyl cellulose, sodium carboxymethyl cellulose, guar gum, gelatin, polyvinyl alcohol, methyl cellulose, hydroxypropyl cellulose, hydroxypropyl-methyl cellulose, and polyethylene oxide.

20. The method of claim 1, wherein the concentration of said hydrogel forming substance in said tablet ranges from 5 to 70% by mass.

* * * * *